United States Patent
Hovnanian et al.

(10) Patent No.: US 9,340,783 B2
(45) Date of Patent: May 17, 2016

(54) EXON SKIPPING THERAPY FOR DYSTROPHIC EPIDERMOLYSIS BULLOSA

(71) Applicants: INSERM (INSTITUT NATIONAL DE LA SANTE ET DE LA RECHERCHE MEDICALE), Paris (FR); UNIVERSITE PARIS DESCARTES, Paris (FR)

(72) Inventors: Alain Hovnanian, Paris (FR); Matthias Titeux, Paris (FR); Sandrina Turczynski, Paris (FR)

(73) Assignees: INSERM (INSTITUT NATIONAL DE LA SANTE ET DE LA RECHERCHE MEDICALE, Paris (FR); UNIVERSITE PARIS DESCARTES, Paris (FR)

( * ) Notice: Subject to any disclaimer, the term of this patent is extended or adjusted under 35 U.S.C. 154(b) by 63 days.

(21) Appl. No.: 14/350,921

(22) PCT Filed: Oct. 11, 2012

(86) PCT No.: PCT/EP2012/070154
§ 371 (c)(1),
(2) Date: Apr. 10, 2014

(87) PCT Pub. No.: WO2013/053819
PCT Pub. Date: Apr. 18, 2013

(65) Prior Publication Data
US 2014/0288155 A1    Sep. 25, 2014

(30) Foreign Application Priority Data
Oct. 11, 2011  (EP) .................................. 11306316

(51) Int. Cl.
*C07H 21/02* (2006.01)
*C07H 21/04* (2006.01)
*A61K 31/70* (2006.01)
*C12N 15/113* (2010.01)
*C12Q 1/68* (2006.01)
*A61K 31/711* (2006.01)

(52) U.S. Cl.
CPC ............. *C12N 15/113* (2013.01); *A61K 31/711* (2013.01); *C12N 2310/11* (2013.01); *C12N 2310/315* (2013.01); *C12N 2310/321* (2013.01); *C12N 2310/346* (2013.01); *C12N 2320/33* (2013.01)

(58) Field of Classification Search
None
See application file for complete search history.

(56) References Cited

U.S. PATENT DOCUMENTS

| 8,524,880 B2 * | 9/2013 | Wilton et al. ................ 536/24.5 |
| 2004/0092464 A1 | 5/2004 | Bennett et al. |
| 2004/0096833 A1 | 5/2004 | Chiang et al. |
| 2007/0054869 A1 | 3/2007 | Bennett et al. |

OTHER PUBLICATIONS

Maki et al., "Targeted Skipping of a Single Exon Harboring a Premature Termination Codon Mutation: Implications and Potential for Gene Correction Therapy for Selective Dystrophic Epidermolysis Bullosa Patients", Journal of Investigative Dermatology, Jun. 15, 2006, pp. 2614-2620, vol. 126, No. 12.

Ningning et al., "Mutation analysis and characterization of COL7A1 mutations in dystrophic epidermolysis bullosa", Experimental Dermatology, Jul. 1, 2008, pp. 553-568, vol. 17, No. 7.

* cited by examiner

*Primary Examiner* — Sean McGarry
(74) *Attorney, Agent, or Firm* — Whitham, Curtis, Christofferson & Cook, P.C.

(57) ABSTRACT

The present invention also relates to an antisense oligonucleotide complementary to a nucleic acid sequence of COL7A1 gene that is necessary for correct splicing of one or more exons which encode amino acid sequence of type VII collagen implicated in dysfunction of a mutated type VII collagen wherein said exons are selected from the group consisting of exon 73, 74 or 80 of the COL7A1 gene. The present invention also relates to a method for the treatment of a patient suffering from Dystrophic Epidermolysis Bullosa caused by a dysfunction of a mutated type VII collagen, comprising the step of administering to said patient a least one antisense oligonucleotide according to the invention.

7 Claims, 5 Drawing Sheets

EXON SKIPPING THERAPY FOR DYSTROPHIC EPIDERMOLYSIS BULLOSA

FIELD OF THE INVENTION

Figure 1:
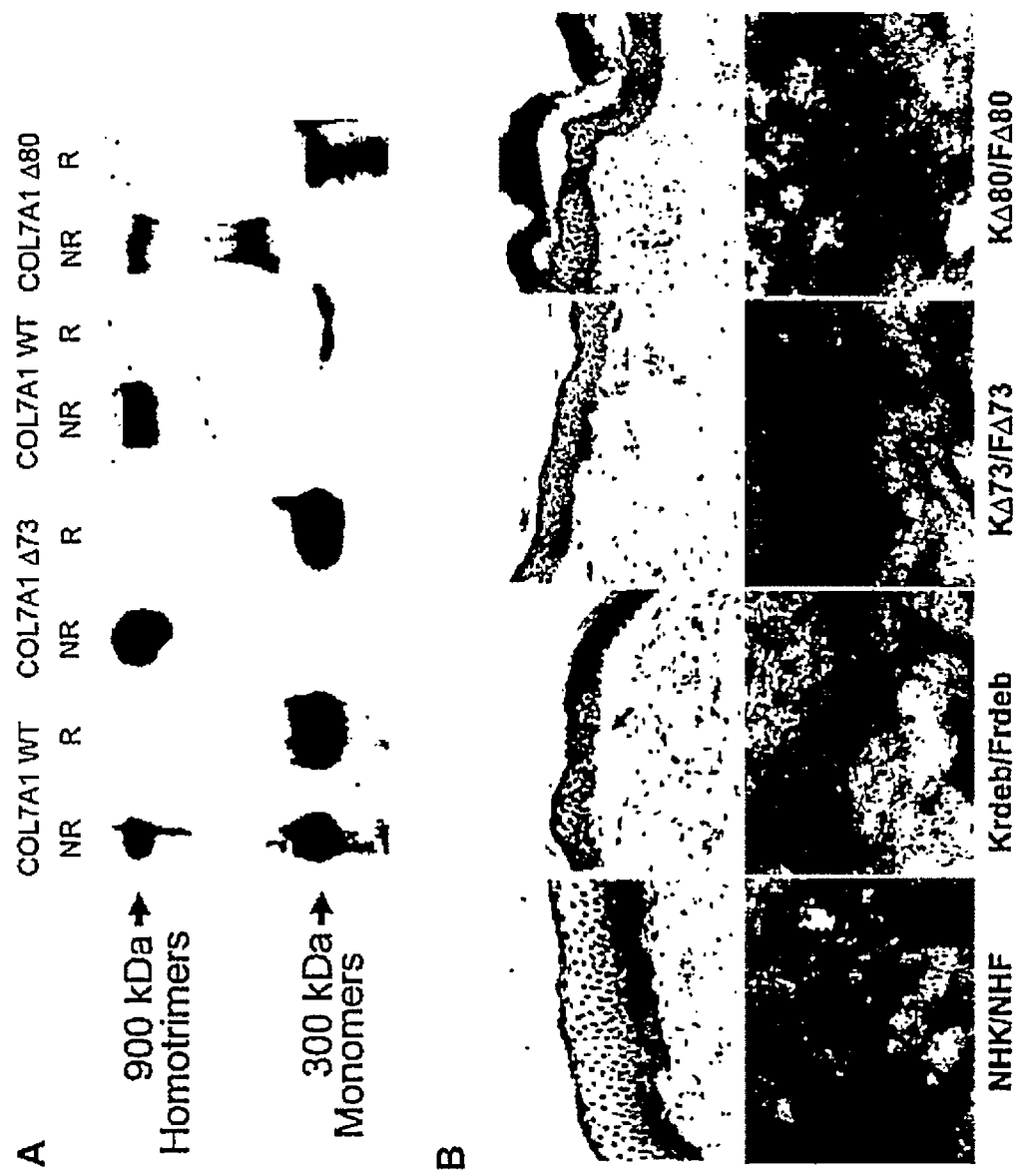

The present invention relates to the treatment of Dystrophic Epidermolysis Bullosa. Particularly, exon skipping strategy is used.

BACKGROUND OF THE INVENTION

Epidermolysis bullosa is a group of inherited mechanobullous disorders characterized by fragility of the skin within the cutaneous basement membrane zone, with considerable clinical and genetic heterogeneity, inherited either in an autosomal dominant or autosomal recessive fashion. Traditionally, EB has been divided into three broad categories based on the level of tissue separation, determined by diagnostic electron microscopy and/or immunoepitope mapping (Fine et al., 2000): the simplex forms of EB (EBS) demonstrate tissue separation within the basal keratinocytes at the bottom layer of epidermis; the junctional forms of EB (JEB) display cleavage within the lamina lucida in the dermoepidermal basement membrane; and in the dystrophic forms (DEB), tissue separation occurs below the lamina densa within the upper papillary dermis (Varki et al., 2007).

DEB is caused by mutations in COL7A1 (OMIM *120120), on chromosomal region 3p21, encoding type VII collagen. It is either dominantly or recessively inherited. The recessive form, RDEB (OMIM #226600) is one of the most severe genodermatoses in children and young adults. The dominant form, DDEB (OMIM #131750) is usually less severe. DEB patients suffer since birth from loss of adhesion between the epidermis and the dermis resulting in severe blistering of the skin and mucosae after mild trauma. The disease leads to severe local and systemic complications, and the prognosis is poor because of the increased risk of aggressive skin cancer. Indeed, over 50% of affected individuals will die before the age of 40-years directly due to metastatic squamous cell carcinoma (Fine et al., 2000). There are 4 subtypes of RDEB: the severe generalized type (Hallopeau-Siemens) which is the most severe, the generalised non-severe (mitis) form, the inversa form (which involves mainly the flexures), and the centripetalis (localised) form. All these clinical variants are caused by loss of function mutations in COL7A1, which result in structural defects in anchoring fibrils (Hilal et al., 1993; Hovnanian et al., 1992). Type VII collagen is the major component of anchoring fibrils which are key attachment structures for dermo-epidermal adhesion.

Type VII collagen is synthesized as a 290-kDa protein precursor. The protein has a homotrimeric quaternary structure, and each of the three identical α1-chains consists of three major domains: the 130-kDa globular, non collagenous domain 1 (NC1) at the amino terminus, the helical, collagenous domain of 140 kDa, and the small non collagenous domain 2 (NC2) at the carboxy terminus. In the extracellular matrix, type VII collagen further assembles into antiparallel dimers, with the helical portions disulfide-bonded at a short carboxy terminal overlap that places the amino terminal globular domains at opposite ends. The NC1 globular domain is encoded by exons 2 to 27. The central collagenous domain is encoded by exons 28 to 112 and folds into an interrupted collagen triple helix. The larger interruption in the periodic Gly-X-X collagenous sequence is the so-called hinge segment, encoded by exons 71 and 72. With a predicted α-helical structure, it is thought to confer flexibility to the molecule. The NC2 domain is encoded by exons 113 to 118. The NC2 domain is required for the trimerisation of the a1 chains and for the antiparallel dimerisation of the homotrimers.

The gene encoding type VII collagen, COL7A1, is segmented into 118 exons and spreads over 32 kb on human chromosome 3p21. The shortest exons are 27-nucleotides long while the longest attains a length of 201 nucleotides. Computational analysis of the genomic sequence revealed that COL7A1 is particularly suited for exon skipping strategy. Among the 118 exons, exons 28 to 112 are in frame, which means that skipping of any of these exons while preserving the reading frame of the mRNA is theoretically feasible.

No specific treatment is available for Dystrophic Epidermolysis Bullosa but the targeted removal of exons carrying recurrent mutations shows therapeutic potential.

SUMMARY OF THE INVENTION

The present invention relates to a method for restoring the function of a mutated type VII collagen comprising the step of preventing splicing of one or more exons which encode amino acid sequence of type VII collagen implicated in dysfunction of a mutated type VII collagen wherein said exons are selected from the group consisting of exon 73, 74 or 80 of the COL7A1 gene.

The present invention also relates to an antisense oligonucleotide complementary to a nucleic acid sequence of COL7A1 gene that is necessary for correct splicing of one or more exons which encode amino acid sequence of type VII collagen implicated in dysfunction of a mutated type VII collagen wherein said exons are selected from the group consisting of exon 73, 74 or 80 of the COL7A1 gene.

Finally the present invention relates to a method for the treatment of a patient suffering from Dystrophic Epidermolysis Bullosa caused by a dysfunction of a mutated type VII collagen, comprising the step of administering to said patient a least one antisense oligonucleotide according to the invention.

DETAILED DESCRIPTION OF THE INVENTION

The inventors hypothesized that exon-skipping strategy could be used for the treatment of Dystrophic Epidermolysis Bullosa and considered exon 73, 74 or 80 as preferential targets for said treatment. Exons 73, 74 and 80 are indeed of particular interest because they carry many recurrent recessive or dominant mutations in COL7A1. Moreover, these exons encode multiples of the Gly-X-X collagenous repeat, so that the shortening of the protein sequence resulting from exon skipping would preserve the periodicity of the collagenous residues.

DEFINITIONS

Throughout the specification, several terms are employed and are defined in the following paragraphs.

The term "protein dysfunction" refers to a loss of function of a protein inducing an abnormal phenotype.

The term "antisense oligonucleotide" refers to a single strand of DNA or RNA that is complementary to a chosen sequence.

The term "type VII collagen" has its general meaning in the art and refers to a protein encoded by the COL7A1 gene. The type VII collagen fibril, composed of three identical alpha collagen chains, is restricted to the basement zone beneath stratified squamous epithelia. It functions as an anchoring fibril between the external epithelia and the underlying stroma. Mutations in this gene are associated with all forms of dystrophic epidermolysis bullosa. The term may include naturally occurring "type VII collagen" and variants and modified forms thereof. The type VII collagen can be from any source, but typically is a mammalian (e.g., human and non-human primate) type VII collagen, particularly a human type VII collagen. An exemplary native human nucleotide sequence encoding for type VII collagen is provided in GenBank database under accession number GenBank/EMBL L23982.

In the context of the invention, the term "patient" refers to any subject, preferably a mammal, and more preferably a human, afflicted with a Dystrophic Epidermolysis Bullosa.

In its broadest meaning, the term "treating" or "treatment" refers to reversing, alleviating, inhibiting the progress of, or preventing the disorder or condition to which such term applies, or one or more symptoms of such disorder or condition.

"Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

Exon Skipping Strategy

As will be understood by those skilled in the art, in the cell nucleus, eukaryotic genes are transcribed into pre-messenger RNA (pre-mRNA) which contains both exons and introns. To form mature mRNA, splicing occurs at specific sequences at the borders of exons and introns (splice sites) thereby removing introns and connecting exons to one another to form mRNA, which is translated into protein. Exons can be specifically targeted to prevent their inclusion in mRNA using antisense oligonucleotides having sequences that are specifically complementary to sequences within or at the borders of a targeted exon e.g. complementary to key splicing sequences such as splice donor sites, splice acceptor sites, branch point, Exonic Splicing Enhancers (ESE) or Intronic Splicing Enhancers (ISE). By annealing to these sequences, they interfere with the splicing machinery e.g. by overlapping and masking intron/exon splice junctions, ESE sequences, ISE sequences or branch points thereby modifying splicing reactions so that the targeted exons are not included in the mature mRNA, i.e., the targeted exons are "skipped". The mRNA thus no longer contains the information of the skipped exon(s) and the protein it encodes does not contain an amino acid sequence corresponding to the skipped exon(s). Accordingly, in the present specification, the expression "preventing splicing of one (or more) exon(s)" refers to the induction of a targeted deletion of said exon(s) in mature mRNA by a modification of splicing using the exon skipping strategy.

The invention thus provides methods for restoring the function of mutated proteins of interest using exon skipping technology. The method involves blocking or preventing the incorporation into mature mRNA of one or more targeted exon(s) which encodes amino sequences that are responsible for the protein dysfunction. This is accomplished by exposing the pre-mRNA that includes exons encoding the protein to antisense oligonucleotides (AONs) which are complementary to sequence motifs that are required for correct splicing of the one or more targeted exons. The AONs bind to complementary required sequences in the pre-mRNA and prevent normal splicing. Instead, the targeted exons are excised and are not included in the mature mRNA that is translated into protein, and the amino acid sequences encoded by the targeted exons are missing from the translated protein.

A first object of the present invention relates to a method for restoring the function of a mutated type VII collagen comprising the step of preventing splicing of one or more exons which encode amino acid sequences that cause said type VII collagen dysfunction. In a particular embodiment of the invention, said method for restoring the function of a mutated type VII collagen comprises the step of preventing splicing of at least one exon selected from the group consisting of exon 73, 74 or 80 of the COL7A1 gene.

According to the present invention, one or more exons selected from the group consisting of exon 73, 74 or 80 may be removed in order to restore the functionality of a mutated collagen VII. Those skilled in the art will recognize that the selection of exons for removal as described herein will usually be predicated on the expectation of a beneficial result such as restoration of the protein functionality.

The invention thus provides methods of restoring partial or complete functionality to type VII collagen, e.g. an unstable, defective, dysfunctional, not enough functional or non-functional type VII collagen.

Those skilled in the art will recognize that there are many ways to determine or measure a level of functionality of a protein, and to determine a level of increase or decrease of functionality e.g. in response to a treatment protocol. Such methods include but are not limited to measuring or detecting an activity of the protein, etc. Such measurements are generally made in comparison to a standard or control or "normal" sample. In addition, when the protein's lack of functionality is involved in a disease process, disease symptoms may be monitored and/or measured in order to indirectly detect the presence or absence of a correctly functioning protein, or to gauge the success of a treatment protocol intended to remedy the lack of functioning of the protein.

Particularly, the functionality of type VII collagen can be measured in vitro and/or in vivo by several methods recognized in the art:

The synthesis of type VII collagen following exon skipping can be assessed by western blotting (Titeux et al., 2010). However, due to the small size of the targeted exons, the skipped mRNA synthesizes a protein with an apparent molecular weight similar to that of the wild-type protein (FIG. 1A).

The correct assembly of the al collagen chains into homotrimers can be demonstrated by western blotting under non reducing conditions. The correct proteolytic pattern of type VII collagen homotrimers can be assessed by Pepsin and collagenase digestions followed by western blotting (Titeux et al., 2010).

Colloidal gold migration assay. Cell mobility of treated cells can be assayed on a collagen matrix as RDEB cells display an enhanced motility compared to normal keratinocytes and fibroblasts (Chen et al., 2002).

In vitro adhesion assays. RDEB cells display a defect in adhesion to extracellular matrix components like type I collagen, type IV collagen, fibronectin but nor laminin I (Chen et al., 2002).

Detection of type VII collagen at the dermal epidermal junction by indirect immunohistochemistry using xenograft of treated RDEB skin equivalents grafted onto nude mice (Titeux et al., 2010).

Assessment of anchoring fibrils formation in vivo by transmission electron microscopy (TEM) using xenograft of treated RDEB skin equivalents grafted onto nude mice (Titeux et al., 2010).

Demonstration of the restoration of dermal-epidermal adherence in vivo using xenograft of treated RDEB skin equivalents grafted onto nude mice (Titeux et al., 2010).

In the present case, AONs are used to cause exon skipping resulting in an amelioration of Dystrophic Epidermolysis Bullosa symptoms (i.e. restoration of protein function or stability) in the range of 30 to 100%, compared to a non-treated patient case. Such symptoms may be observed on a micro level (i.e. restoration of protein expression and/or localisation evaluated by immunohistochemistry, immunofluorescence, western-blot analyses; amelioration of the skin lesion by histological examination; restoration/amelioration of protein functionality evaluated by the ability to form anchoring fibril between the external epithelia and the underlying stroma . . .

Generally, the removal of exon-encoded sequences from a type VII collagen protein is carried out using anti-sense oligonucleotides (AONs). Oligonucleotides are designed to complement suitable sequences, usually RNA sequences within the pre-mRNA molecule which are required for correct splicing of the targeted exon(s), thereby blocking splicing reactions that would incorporate the targeted exon(s) into mature mRNA. An AON typically binds to the sequence which it complements and hinders the splicing reaction. Sequences are selected so as to be specific, i.e. the AON's are complementary only to the sequences of the pre-mRNA and not to other nucleic acid sequences. The AON's used in the practice of the invention may be of any suitable type, e.g. oligodeoxyribonucleotides, oligoribonucleotides, morpholinos, tricyclo-DNA-antisense oligonucleotides, U7- or U1-mediated AONs or conjugate products thereof such as peptide-conjugated or nanoparticle-complexed AONs. AONs employed in the practice of the invention are generally from about 10 to about 30 nucleotides in length, and may be for example, about 10 or fewer, or about 15, or about 20 or about 30 nucleotides or more in length depending on the targeted sequences and the AON chemistry.

A further object of the invention relates to an antisense oligonucleotide complementary to a nucleic acid sequence of COL7A1 gene that is necessary for correct splicing of one or more exons which encode amino acid sequence of type VII collagen implicated in dysfunction of a mutated type VII collagen. In a particular embodiment, the invention relates to an antisense oligonucleotide of the invention wherein said antisense oligonucleotide is complementary to a nucleic acid sequence comprising or consisting of exon 73, 74 or 80 of the COL7A1 gene. In a more particular embodiment, said antisense oligonucleotides are those depicted in Table 1:

TABLE 1

Sequences of the antisense oligoribonucleotides

| Name | Sequence (5'-3') |
| --- | --- |
| ESE73.3 | UCUCCACGGUCGCCCUUCAGCCCGCGUUCU (SEQ ID NO: 1) |
| ESE73.7 | UCUCCACGGUCGCCCUUCAGCCCGC (SEQ ID NO: 2) |
| SA + ESE-74 | CCUUUCUCUCCCCGUUCUCCCUGAA (SEQ ID NO: 3) |
| SA + ESE-74_R2063W | CCUUUCUCUCCCCAUUCUCCCUGAA (SEQ ID NO: 4) |
| ESE-74.2 + SD | CCACCUGUUCUCCACGUUCUCCUUUC (SEQ ID NO: 5) |

TABLE 1 -continued

Sequences of the antisense oligoribonucleotides

| Name | Sequence (5'-3') |
| --- | --- |
| ESE-80.3 | GGCCUCUUGGACCCUGCAGACCCU (SEQ ID NO: 6) |
| ESE80-3_Q2170X | GGCCUCUUGGACCCUACAGACCCU (SEQ ID NO: 7) |

Figure 2:
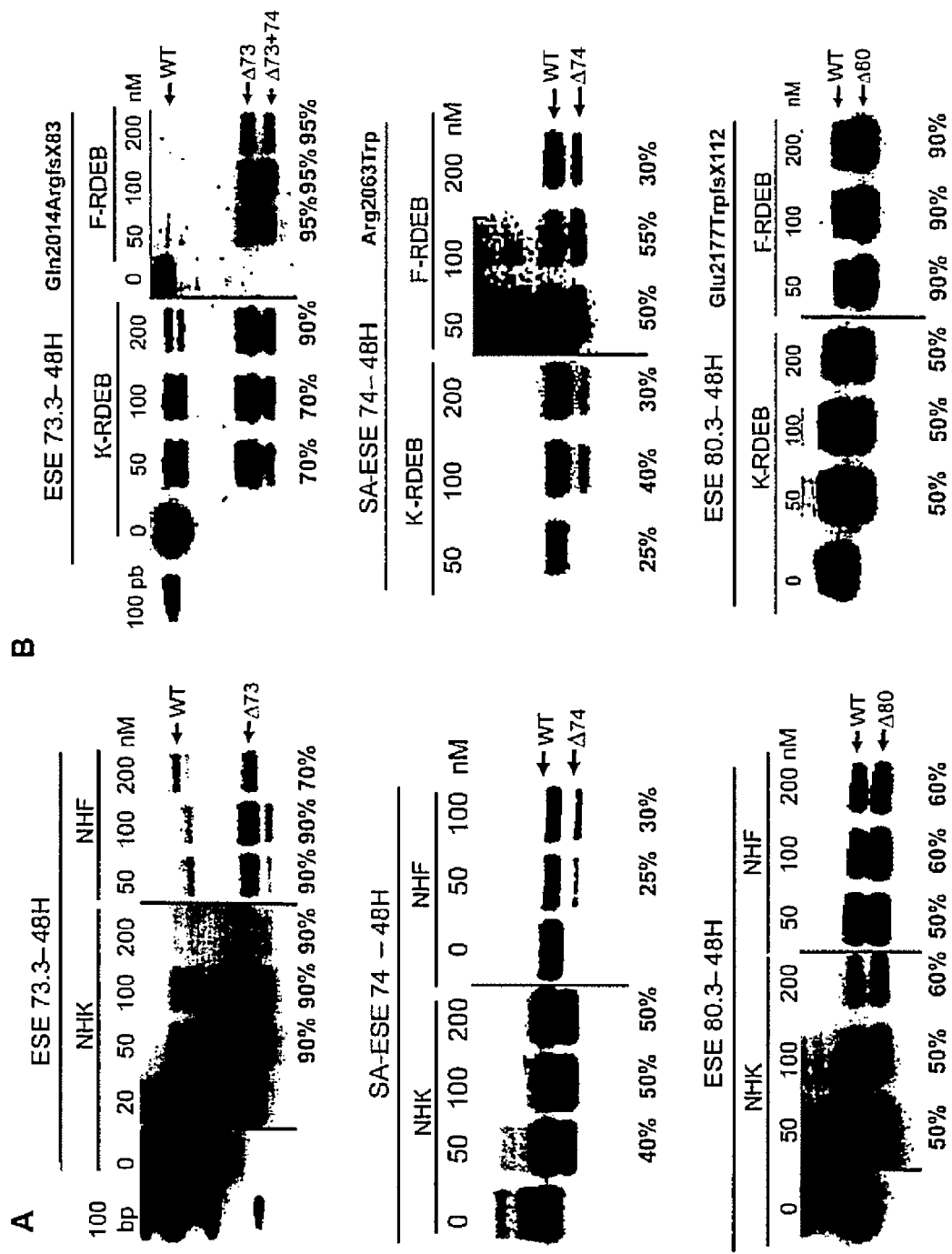

In one embodiment, antisense oligonucleotide ESE73.3 and ESE73.7 are particularly suitable for preventing splicing of exon 73 (FIG. 2).

In one embodiment SA+ESE-74, SA+ESE-74_R2063W are particularly suitable for preventing splicing of exon 74 (FIG. 2).

In one embodiment ESE-80.3 and ESE80-3_Q2170X are particularly suitable for preventing splicing of exon 80 (FIG. 2).

For use in the instant invention, the AONs of the invention can be synthesized de novo using any of a number of procedures well known in the art. For example, the b-cyanoethyl phosphoramidite method; nucleoside H-phosphonate method. These chemistries can be performed by a variety of automated nucleic acid synthesizers available in the market. These nucleic acids may be referred to as synthetic nucleic acids.

For use in vivo, the AONs may be or are stabilized. AON stabilization can be accomplished via phosphate backbone modifications. Preferred stabilized AON's of the instant invention have a modified backbone, e.g. have phosphorothioate linkages to provide maximal activity and protect the AON from degradation by intracellular exo- and endo-nucleases. Other possible stabilizing modifications include phosphodiester modifications, combinations of phosphodiester and phosphorothioate modifications, methylphosphonate, methylphosphorothioate, phosphorodithioate, p-ethoxy, and combinations thereof. Chemically stabilized, modified versions of the AON's also include "Morpholinos" (phosphorodiamidate morpholino oligomers, PMOs), 2'-O-Met oligomers, tricyclo (tc)-DNAs, U7 short nuclear (sn) RNAs, or tricyclo-DNA-oligoantisense molecules (U.S. Provisional Patent Application Ser. No. 61/212,384 For: Tricyclo-DNA Antisense Oligonucleotides, Compositions and Methods for the Treatment of Disease, filed Apr. 10, 2009, the complete contents of which is hereby incorporated by reference. Other forms of AONs that may be used to this effect are AON sequences coupled to small nuclear RNA molecules such as U1 or U7 in combination with a viral transfer method based on, but not limited to, lentivirus or adeno-associated virus.

In another particular embodiment, the antisense oligonucleotides of the invention are 2'-O-methyl-phosphorothioate nucleotides.

Antisense sequences of the invention may be delivered in vivo alone or in association with a vector. In its broadest sense, a "vector" is any vehicle capable of facilitating the transfer of the antisense sequence to the cells and preferably cells expressing collagen VII. Preferably, the vector transports the nucleic acid to cells with reduced degradation relative to the extent of degradation that would result in the absence of the vector. In general, the vectors useful in the invention include, but are not limited to, plasmids, phagemids, viruses, other vehicles derived from viral or bacterial sources that have been manipulated by the insertion or incorporation of the antisense oligonucleotides sequences.

Viral vectors are a preferred type of vector and include, but are not limited to nucleic acid sequences from the following viruses: lentivirus such as HIV-1, retrovirus, such as moloney murine leukemia virus, adenovirus, adeno-associated virus; SV40-type viruses; Herpes viruses such as HSV-1 and vaccinia virus. One can readily employ other vectors not named but known to the art. Among the vectors that have been validated for clinical applications and that can be used to deliver the antisense sequences, lentivirus, retrovirus and AAV show a greater potential for exon skipping strategy.

Retrovirus-based and lentivirus-based vectors that are replication-deficient (i.e., capable of directing synthesis of the desired proteins, but incapable of manufacturing an infectious particle) have been approved for human gene therapy trials. They have the property to integrate into the target cell genome, thus allowing for a persistent transgene expression in the target cells and their progeny.

The human parvovirus Adeno-Associated Virus (AAV) is a dependovirus that is naturally defective for replication which is able to integrate into the genome of the infected cell to establish a latent infection. The last property appears to be unique among mammalian viruses because the integration occurs at a specific site in the human genome, called AAVS1, located on the chromosome 19 (19q13.3-qter). AAV-based recombinant vectors lack the Rep protein, AAV vectors and integrate with low efficacy and low specificity into the host genome, and are mainly present as stable circular episomes that can persists for months and maybe years in the target cells. Therefore AAV has aroused considerable interest as a potential vector for human gene therapy. Among the favourable properties of the virus are its lack of association with any human disease and the wide range of cell lines derived from different tissues that can be infected. Actually 12 different AAV serotypes (AAV 1 to 12) are known, each with different tissue tropisms (Wu et al., 2006). Nonetheless, AAV are very valuable vectors which are now extensively used to transfer small antisens sequences to selectively knock-down alleles or modulate the splicing of target genes (Goyenvalle et al., 2004; Xia et al., 2004).

Other vectors include plasmid vectors. Plasmid vectors have been extensively described in the art and are well known to those skilled in the art. See e.g. Sambrook et al., 1989. In the last few years, plasmid vectors have been used as DNA vaccines for delivering antigen-encoding genes to cells in vivo. They are particularly advantageous for this because they do not have the same safety concerns as with many of the viral vectors. Plasmids may be delivered by a variety of parenteral, mucosal and topical routes. For example, the DNA plasmid can be injected by intradermal, subcutaneous, or other routes. It may also be administered into the epidermis or a mucosal surface using a gene-gun. The plasmids may be given in an aqueous solution, dried onto gold particles or in association with another DNA delivery system including but not limited to liposomes, dendrimers, cochleate and microencapsulation.

In a preferred embodiment, the vectorized antisense sequences are fused with a small nuclear RNA (snRNA) such as U7 or U1 in order to ensure their stability and spliceosome targeting (Goyenvalle et al., 2004; Montgomery and Dietz, 1997).

Methods of Treatment and Pharmaceutical Compositions

A further object of the present invention relates to a method for the treatment of patients suffering from DEB comprising the step of administering to said patient antisense oligonucleotides complementary to nucleic acid sequences that are necessary to modulate the splicing of at least one exon selected from the group consisting of exon 73, 74 or 80 of COL7A1 gene. According to the present invention, one or more exons selected from the group consisting of exon exon 73, 74 or 80 may be removed in order to restore the functionality of a mutated collagen VII. In a more particular embodiment, said antisense oligonucleotides are those depicted in Table 1 and may be associated with a vector as above described.

In another particular embodiment of the invention, said patient harbours a mutation in exon 73, and/or 74, and/or 80 of COL7A1 gene. Said mutation leads to a type VII collagen dysfunction in said patient.

The invention further relates to an antisense oligonucleotide of the invention (or a vector comprising thereof) for the treatment of Dystrophic Epidermolysis Bullosa.

The present invention also provides a pharmaceutical composition containing at least one antisense oligonucleotide of the invention (or a vector comprising thereof) for the treatment of a Dystrophic Epidermolysis Bullosa.

In addition to AONs (or a vector comprising thereof), pharmaceutical compositions of the present invention may also include a pharmaceutically or physiologically acceptable carrier such as saline, sodium phosphate, etc. The compositions will generally be in the form of a liquid, although this need not always be the case. Suitable carriers, excipients and diluents include lactose, dextrose, sucrose, sorbitol, mannitol, starches, gum acacia, calcium phosphates, alginate, tragacanth, gelatin, calcium silicate, microcrystalline cellulose, polyvinylpyrrolidone, celluose, water syrup, methyl cellulose, methyl and propylhydroxybenzoates, mineral oil, etc. The formulations can also include lubricating agents, wetting agents, emulsifying agents, preservatives, buffering agents, etc. In particular, the present invention involves the administration of AONs (or vectors comprising thereof) and is thus somewhat akin to gene therapy. Those skilled in the art will recognize that nucleic acids are often delivered in conjunction with lipids (e.g. cationic lipids or neutral lipids, or mixtures of these), frequently in the form of liposomes or other suitable micro- or nano-structured material (e.g. micelles, lipocomplexes, dendrimers, emulsions, cubic phases, etc.).

The compositions of the invention are generally administered by injection, e.g. intravenously, subcutaneously or intramuscularly. However topical administration of the composition may be preferred.

Injectable preparations, for example, sterile injectable aqueous or oleaginous suspensions may be formulated according to the known art using suitable dispensing or wetting agents and suspending agents. The sterile injectable preparation can also be a sterile injectable solution or suspension in a nontoxic parenterally acceptable diluent or solvent, for example, as a solution in 1,3-butanediol.

In a particular embodiment, it may be desirable to administer the antisense oligonucleotides of the invention ((or a vector comprising thereof) in admixture with a topical pharmaceutically acceptable carrier. The topical pharmaceutically acceptable carrier is any substantially nontoxic carrier conventionally usable for topical administration of pharmaceuticals in which the antisense oligonucleotides of the invention (or a vector comprising thereof) will remain stable and bioavailable when applied directly to skin surfaces. For example, carriers such as those known in the art effective for penetrating the keratin layer of the skin into the stratum corneum may be useful in delivering the antisense oligonucleotides of the invention (or a vector comprising thereof) to the area of interest. Such carriers include liposomes. Antisense oligonucleotides of the invention (or a vector comprising thereof) can be dispersed or emulsified in a medium in a conventional manner to form a liquid preparation or mixed with a semi-solid (gel) or solid carrier to form a paste, powder, ointment, cream, lotion or the like.

Suitable topical pharmaceutically acceptable carriers include water, buffered saline, petroleum jelly (vaseline), petrolatum, mineral oil, vegetable oil, animal oil, organic and inorganic waxes, such as microcrystalline, paraffin and ozocerite wax, natural polymers, such as xanthanes, gelatin, cellulose, collagen, starch, or gum arabic, synthetic polymers, alcohols, polyols, and the like. The carrier can be a water miscible carrier composition. Such water miscible, topical pharmaceutically acceptable carrier composition can include those made with one or more appropriate ingredients outset of therapy.

Because dermatologic conditions to be treated may be visible, the topical carrier can also be a topical acceptable carrier. The topical acceptable carrier will be any substantially non-toxic carrier conventionally usable for topical administration in which antisense oligonucleotides of the invention will remain stable and bioavailable when applied directly to the skin surface. Suitable cosmetically acceptable carriers are known to those skilled in the art and include, but are not limited to, cosmetically acceptable liquids, creams, oils, lotions, ointments, gels, or solids, such as conventional cosmetic night creams, foundation creams, suntan lotions, sunscreens, hand lotions, make-up and make-up bases, masks and the like. Topical acceptable carriers may be similar or identical in nature to the above described topical pharmaceutically acceptable carriers.

It may be desirable to have a delivery system that controls the release of antisense oligonucleotides of the invention to the skin and adheres to or maintains itself on the skin for an extended period of time to increase the contact time of the antisense oligonucleotides of the invention (or a vector comprising thereof) on the skin. Sustained or delayed release of antisense oligonucleotides of the invention (or a vector comprising thereof) provides a more efficient administration resulting in less frequent and/or decreased dosage of antisense oligonucleotides of the invention (or a vector comprising thereof) and better patient compliance. Examples of suitable carriers for sustained or delayed release in a moist environment include gelatin, gum arabic, xanthane polymers. Pharmaceutical carriers capable of releasing the antisense oligonucleotides of the invention when exposed to any oily, fatty, waxy, or moist environment on the area being treated, include thermoplastic or flexible thermoset resin or elastomer including thermoplastic resins such as polyvinyl halides, polyvinyl esters, polyvinylidene halides and halogenated polyolefins, elastomers such as brasiliensis, polydienes, and halogenated natural and synthetic rubbers, and flexible thermoset resins such as polyurethanes, epoxy resins and the like. Controlled delivery systems are described, for example, in U.S. Pat. No. 5,427,778 which provides gel formulations and viscous solutions for delivery of the antisense oligonucleotides of the invention (or a vector comprising thereof) to a skin site. Gels have the advantages of having a high water content to keep the skin moist, the ability to absorb skin exudate, easy application and easy removal by washing. Preferably, the sustained or delayed release carrier is a gel, liposome, microsponge or microsphere. The antisense oligonucleotides of the invention (or a vector comprising thereof) can also be administered in combination with other pharmaceutically effective agents including, but not limited to, antibiotics, other skin healing agents, and antioxidants.

One skilled in the art will recognize that the amount of an AON (or a vector comprising thereof) to be administered will be an amount that is sufficient to induce amelioration of unwanted disease symptoms. Such an amount may vary inter alia depending on such factors as the gender, age, weight, overall physical condition, of the patient, etc. and may be determined on a case by case basis. The amount may also vary according to the type of condition being treated, and the other components of a treatment protocol (e.g. administration of other medicaments such as steroids, etc.). Generally, a suitable dose is in the range of from about 1 mg/kg to about 100 mg/kg. If a viral-based delivery of AONs is chosen, suitable doses will depend on different factors such as the viral strain that is employed, the route of delivery (intramuscular, intravenous, intra-arterial or other), but may typically range from 10e10 to 10e12 viral particles/kg. Those skilled in the art will recognize that such parameters are normally worked out during clinical trials. Further, those skilled in the art will recognize that, while disease symptoms may be completely alleviated by the treatments described herein, this need not be the case. Even a partial or intermittent relief of symptoms may be of great benefit to the recipient. In addition, treatment of the patient is usually not a single event. Rather, the AONs of the invention will likely be administered on multiple occasions, that may be, depending on the results obtained, several days apart, several weeks apart, or several months apart, or even several years apart.

The invention will be further illustrated by the following figures and examples. However, these examples and figures should not be interpreted in any way as limiting the scope of the present invention.

FIGURES

FIG. 1. Demonstration of the functionality of type VII collagen deleted of exon 73 or 80. A) Wild type type VII collagen or deleted forms lacking exon 73 or 80 analyzed on a 4-12% gradient gel under non reducing conditions (NR) or after reduction with β-mercaptoethanol (R), showing the presence of both monomers (M, 300 kDa) and homotrimers (H, ~900 kDa) of type VII collagen. B) Human skin equivalent (SE) xenografts analysed by immunohistochemistry and transmission electron microscopy showing normal type VII collagen deposition along the dermal-epidermal junction; anchoring fibrils formation (red arrowheads) and dermal-epidermal adhesion in SE made of normal cells (NHK/NHF) and cells expressing deleted forms (KA73/FA73 and KA80/FA80) but not in SE made of unmodified RDEB cells (Krdeb/Fdreb). Note the characteristic blistering (arrow).

FIG. 2. Demonstration of the exon skipping efficiency in vitro. Dose response experiments of 3 antisense oligoribonucleotides targeting exon 73, exon 74 or exon 80 of COL7A1 (see table 1). RT-PCR were performed on total RNA extracted 48H after transfection of 20 to 200 nM of the 2'O-Methyl Phosphorothioate oligoribonucleotides on normal human keratinocytes and fibroblasts (A) and on RDEB keratinocytes and fibroblasts (B). The mutation on the targeted messenger RNA is indicated in red. Wild type and skipped amplimers are indicated. Gel densitometry demonstrated a skipping efficiency ranging from 40 to 90% depending on the targeted exon and the amount of the antisense.

Figure 3:
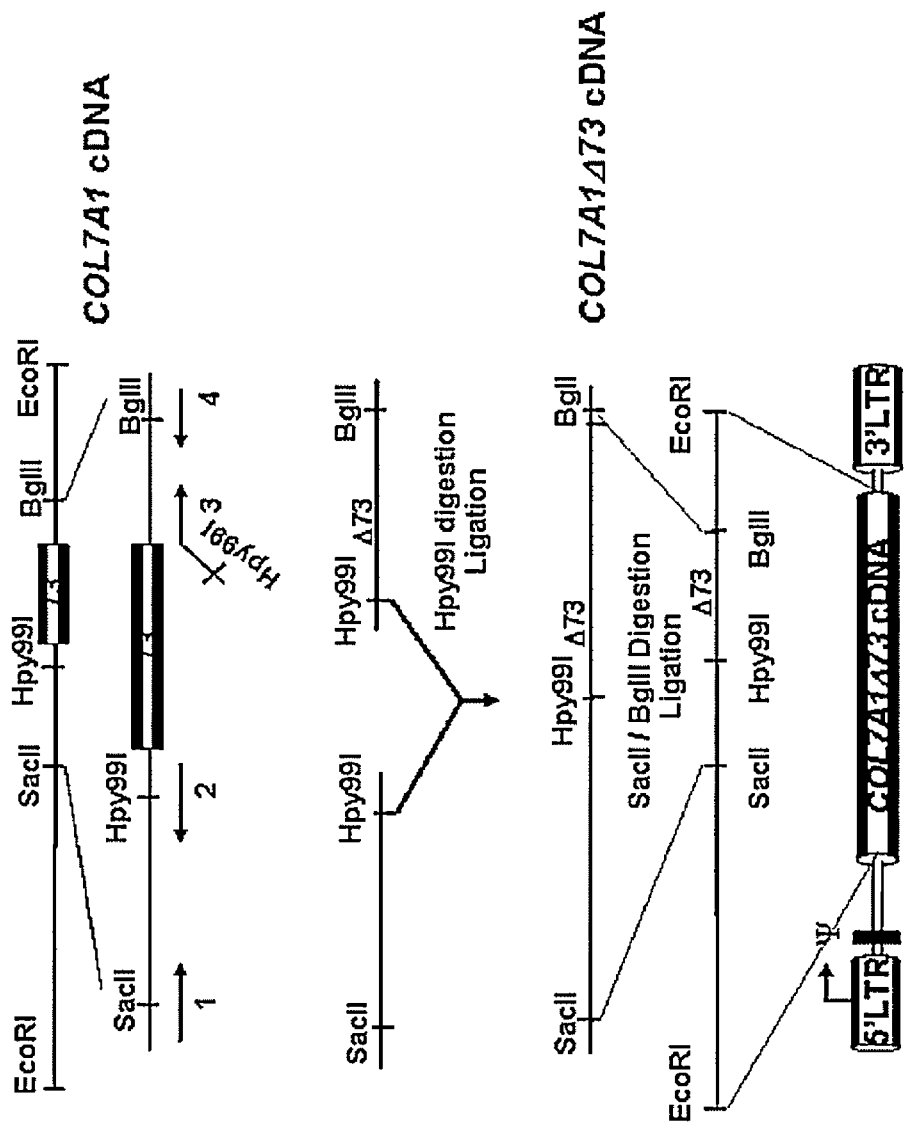

FIG. 3. Cloning of a type VII collagen cDNA deleted of the exon 73 sequence into a MSCV retroviral vector backbone. The same strategy was used to generate the MSCV-COL7A1Δ80 vector.

Figure 4:
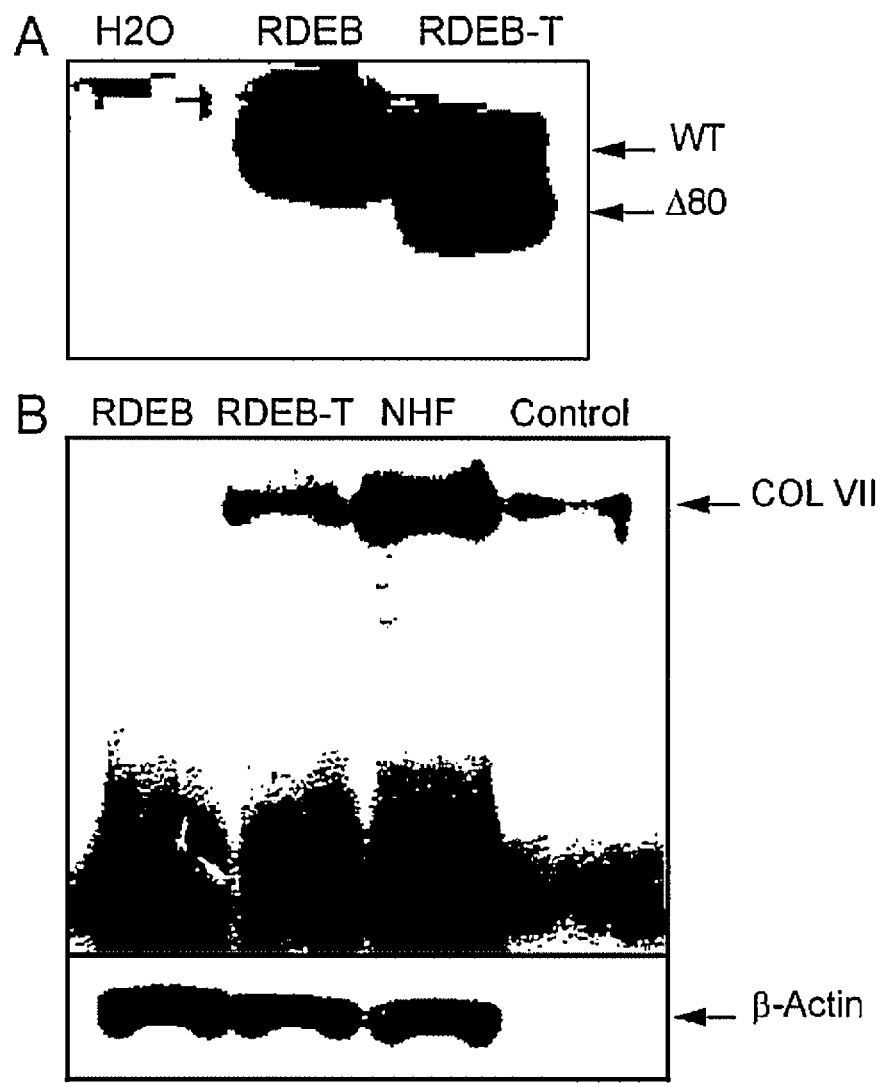

FIG. 4. In vitro demonstration of type VII collagen re-expression following exon skipping in RDEB fibroblasts. RDEB primary fibroblasts from a patient carrying a homozygous nonsense mutation (p.Gln2170Term) were treated with AON ESE80.3 to induce in frame exon 80 skipping. A) RT- PCR analysis demonstrated high level of exon skipping (~85%) in transfected RDEB fibroblasts (RDEB-T) compared to non-treated cells (RDEB). B) Western-blot analysis demonstrated strong type VII collagen expression in treated cells (RDEB-T) compared to non-transfected fibroblasts (RDEB). Expression in RDEB-T cells was estimated to be up to 20% of the normal amount as compared with normal human fibroblasts protein extracts.

Figure 5:
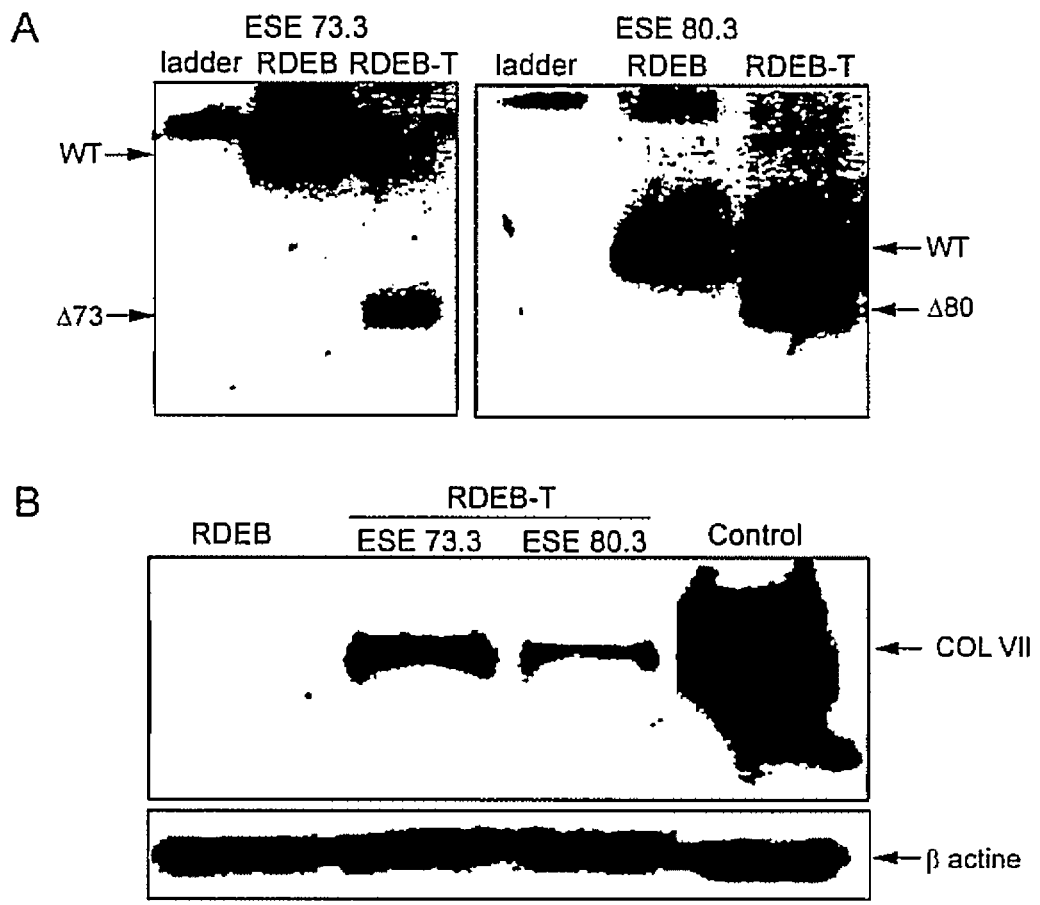

FIG. 5. In vitro demonstration of type VII collagen re-expression following exon skipping in RDEB keratinocytes. RDEB primary keratinocytes from a patient compound heterozygous for frame-shift mutations in exon 73 and in exon 80 were treated with AON ESE 73.3 and AON ESE80.3 to induce in frame exon skipping of exons 73 and 80, respectively. A) RT-PCR analysis demonstrated high level of exon skipping in transfected RDEB keratinocytes (RDEB-T) compared to non-treated cells (RDEB). B) Western-blot analysis demonstrated strong type VII collagen expression in treated cells (RDEB-T) compared to non-transfected keratinocytes (RDEB).

EXAMPLE 1

Demonstration of the Functionality of Type VII Collagen Molecules Deleted of the Sequences of the Targeted Exons I-1. Cloning of Deleted COL7A1 cDNAs into Retroviral Vectors.

To demonstrate that skipping of one of these exons preserves the protein function, different deleted type VII collagen cDNAs were cloned into a retroviral vector (FIG. 3). A SacII BglII fragment encompassing exons 58 to 94 was cloned into a PGEM-T vector (Promega) generating the PGEM-COL7A1-SacII/BglII plasmid. Two primers (1 and 2) were designed to amplify a fragment containing exons 58 to 72. Two other primers (3 and 4) were designed to amplify a fragment containing the Hpy99I restriction site at the end of exon 72 to exon 94 but missing the exon 73 sequence. The red line represents the sequence of exon 72 contained in primer 3. After PCR amplification using Pfx proof-reading polymerase (Invitrogen), the fragments were subcloned into PGEM-T vectors, digested using SacII, BglII and Hpy99I and then cloned into the PGEM-COL7A1-SacII/BglII generating a SacII/BglII fragment deleted from the exon 73 sequence. This fragment was subsequently cloned into a MSCV-COL7A1 vector digested by SacII/BglII to generate the MSCV-COL7A1Δ73 retroviral vector. The same approach was used to generate a MSCV-COL7A1Δ80 retroviral vector. MSCV-COL7A1-Δ74 and MSCV-COL7A1Δ73-74 retroviral vectors are currently under construction.

I-2. Production of Retroviral Particles and Transduction of RDEB Keratinocytes.

Amphotropic pseudotyped retroviral vector expressing wild-type COL7A1 cDNA or cDNAs deleted of exons 73 or 80 were produced by transient tri-transfection into HEK 293T cells of a packaging construct encoding the helper functions, a plasmid producing the Amphotropic envelope and the vectors themselves (Zufferey et al., 1997). Culture medium were collected at 24, 48 and 72 hours, pooled, 0.45 µm filtered aliquoted and stored at −80° C. until used. Viral titers were determined by 2 hours transduction period with serial dilutions of the vector preparations of $10^5$ HCT116 cells in a twelve-well plate in the presence of 6 µg/mL polybrene. 72 h later, genomic DNA from transduced cells was extracted using a genomic DNA purification kit (Promega). The infectious particles titer (ip/mL) was determined by quantitative real time PCR using primers and probes specific to the integrated proviruses.

RDEB keratinocytes were plated at a density of 10.000 cells per $cm^2$ in six-well culture dishes. Cells were infected with viral suspensions at a MOI of 20 with polybrene (8 µg/ml). Medium were changed 4 hours later and the cells were cultured in their growth medium. The transduction efficiency was evaluated by immunocytochemistry. A good level of transduction (about 80%) has been achieved with each retroviral vectors.

I-3. Deleted Type VII Collagen Synthesis and Assembly

Culture supernatant of primary RDEB keratinocytes transduced with each retroviral vector expressing wild-type COL7A1 cDNA, COL7A1Δ73 and COL7A1Δ80 cDNAs were submitted to SDS-PAGE and immunoblotted using LH 7.2 antibody (FIG. 1A). Under non reducing condition, bands of 900 kDa corresponding to homotrimers of full-length type VII collagen and deleted type VII collagen were detected. Under reducing conditions, only bands corresponding to monomers of full-length type VII collagen and deleted type VII collagen were seen. Because of the two proteins differs only by 67 amino acids, they display the same apparent molecular weight. This result demonstrates that type VII collagen deleted of exon 73 or exon 80 is secreted and able to homotrimerize.

I-4. Assessment In Vivo Functionality and Anchoring Fibrils Formation

The next step is to demonstrate that homotrimers of deleted type VII collagen are able to assemble into proper anchoring fibrils. For this purpose, skin equivalents made of human keratinocytes and human fibroblasts grafted onto SCID mice are being used. Human skin equivalents grafted onto immunodeficient mice constitute a powerful tool to assess the functional properties of corrected forms of type VII collagen molecules in vivo. The grafted skin equivalents can be maintained on the host mice for several months, allowing human Type VII collagen to build up and organize into anchoring fibrils detectable by Transmission Electron Microscopy (Titeux et al. 2010).

Skin equivalents have been generated using normal primary human keratinocytes (expressing wild type COL7A1), primary RDEB keratinocytes (lacking COL7A1 expression) and genetically engineered primary RDEB keratinocytes (expressing COL7A1Δ73 or COL7A1Δ80) as the epidermal component. In each case, the dermal component is made with RDEB primary fibroblasts lacking type VII collagen expression. They have then be grafted orthopically onto the back of immunodeficient mice. The skin equivalents made from RDEB keratinocytes and normal human keratinocytes serve as negative and positive control respectively (FIG. 1B).

These results demonstrate clearly that type VII collagen deleted of the sequences encoded by exon 73 and 80 is functional in vivo.

EXAMPLE 2

Demonstration of Efficient Skipping of Selected COL7A1 Exons In vitro

Once the demonstration that COL7A1 deleted of sequences encoded by the targeted exons is functional, we have induced the targeted removal of these exons using AONs.

We have selected over 16 different antisense sequences targeting key splice elements in the selected exons and surrounding introns: donor/acceptor splice sites, branch-point and ESEs as predicted in silico by ESE-finder or RESCUE-ESE softwares (Cartegni et al., 2003; Fairbrother et al., 2002).

The AONs used was 2'O-Methyl-phosphorothioate modified ribonucleotides. The length and ΔG of self-annealing or dimerization were important factors affecting the AONs efficiency. Resulting best AON sequences are listed in Table I.

These AONs were transfected using lipofectamine 2000 (Invitrogen) in cultured primary normal and RDEB keratinocytes and fibroblasts at escalading doses ranging from 50 nM up to 200 nM. Results show that exon skipping efficiency range between 50 up to 95% onto primary patient cells as demonstrated by densitometry after RT-PCR experiments (FIG. 2).

EXAMPLE 3

Demonstration of Functional Correction In Vitro Following Exon Skipping

In vitro demonstration of the restoration of type VII collagen functionality following exon skipping can be performed by Western-blot analyses. Fibroblasts of a patient carrying a homozygous nonsense mutation in exon 80 (p.Gln2170Term) have been transfected with the ESE80.3 2'O-methyl oligoribonucleotide (50 nM). Total RNA and total protein were extracted 72 h later. RNA was subjected to RT-PCR to demonstrate in-frame skipping and proteins were subjected to SDS-PAGE and Western-blotting (FIG. 4). A high exon skipping efficiency (~85%) was demonstrated by RT-PCR and gel densitometry (FIG. 4A). The western blot analysis revealed a strong re-expression of type VII collagen in the RDEB cells after 72 h of treatment with the AON (RDEB-T) compared to non transfected RDEB fibroblasts (RDEB). Type VII collagen expression was estimated to 20% of the amount in normal human fibroblasts (NHF) after only 3 days of treatment.

Similarly, keratinocytes from a patient compound heterozygous for frameshift mutations in exons 73 (p.Gln2014ArgfsX83) and 80 (p.Gly2177TrpfsX112) were treated with 50 nM of ESE 73.3 or 50 nM of ESE 80.3 to induce in frame skipping of exons 73 and 80 (FIG. 5). Western blot analysis demonstrated strong re-expression of type VII collagen protein (FIG. 5B), stronger in the cells treated with ESE 73.3 in accordance with the exon skipping efficiency demonstrated by RT-PCR (FIG. 5A).

REFERENCES

Throughout this application, various references describe the state of the art to which this invention pertains. The disclosures of these references are hereby incorporated by reference into the present disclosure.

Cartegni, L., Wang, J., Zhu, Z., Zhang, M. Q., and Krainer, A. R. (2003). ESEfinder: A web resource to identify exonic splicing enhancers. Nucleic Acids Res 31, 3568-3571.

Chen, M., Kasahara, N., Keene, D. R., Chan, L., Hoeffler, W. K., Finlay, D., Barcova, M., Cannon, P. M., Mazurek, C., and Woodley, D. T. (2002). Restoration of type VII collagen expression and function in dystrophic epidermolysis bullosa. Nat Genet 32, 670-675.

Fairbrother, W. G., Yeh, R. F., Sharp, P. A., and Burge, C. B. (2002). Predictive identification of exonic splicing enhancers in human genes. Science 297, 1007-1013.

Fine, J. D., Eady, R. A., Bauer, E. A., Briggaman, R. A., Bruckner-Tuderman, L., Christiano, A., Heagerty, A., Hintner, H., Jonkman, M. F., McGrath, J., et al. (2000). Revised classification system for inherited epidermolysis bullosa: Report of the Second International Consensus Meeting on diagnosis and classification of epidermolysis bullosa. J Am Acad Dermatol 42, 1051-1066.

Goyenvalle, A., Vulin, A., Fougerousse, F., Leturcq, F., Kaplan, J. C., Garcia, L., and Danos, O. (2004). Rescue of dystrophic muscle through U7 snRNA-mediated exon skipping. Science 306, 1796-1799.

Hilal, L., Rochat, A., Duquesnoy, P., Blanchet-Bardon, C., Wechsler, J., Martin, N., Christiano, A. M., Barrandon, Y., Uitto, J., Goossens, M., et al. (1993). A homozygous insertion-deletion in the type VII collagen gene (COL7A1) in Hallopeau-Siemens dystrophic epidermolysis bullosa. Nat Genet 5, 287-293.

Hovnanian, A., Duquesnoy, P., Blanchet-Bardon, C., Knowlton, R. G., Amselem, S., Lathrop, M., Dubertret, L., Uitto, J., and Goossens, M. (1992). Genetic linkage of recessive dystrophic epidermolysis bullosa to the type VII collagen gene. J Clin Invest 90, 1032-1036.

Montgomery, R. A., and Dietz, H. C. (1997). Inhibition of fibrillin 1 expression using U1 snRNA as a vehicle for the presentation of antisense targeting sequence. Hum Mol Genet 6, 519-525.

Titeux, M., Pendaries, V., Zanta-Boussif, M. A., Decha, A., Pironon, N., Tonasso, L., Mejia, J. E., Brice, A., Danos, O., and Hovnanian, A. (2010). SIN retroviral vectors expressing COL7A1 under human promoters for ex vivo gene therapy of recessive dystrophic epidermolysis bullosa. Mol Ther 18, 1509-1518.

Varki, R., Sadowski, S., Uitto, J., and Pfendner, E. (2007). Epidermolysis bullosa. II. Type VII collagen mutations and phenotype-genotype correlations in the dystrophic subtypes. J Med Genet 44, 181-192.

Wu, Z., Asokan, A., and Samulski, R. J. (2006). Adeno-associated virus serotypes: vector toolkit for human gene therapy. Mol Ther 14, 316-327.

Xia, H., Mao, Q., Eliason, S. L., Harper, S. Q., Martins, I. H., Orr, H. T., Paulson, H. L., Yang, L., Kotin, R. M., and Davidson, B. L. (2004). RNAi suppresses polyglutamine-induced neurodegeneration in a model of spinocerebellar ataxia. Nat Med 10, 816-820.

Zufferey, R., Nagy, D., Mandel, R. J., Naldini, L., and Trono, D. (1997). Multiply attenuated lentiviral vector achieves efficient gene delivery in vivo. Nat Biotechnol 15, 871-875.

The invention claimed is:

1. A method for restoring the function of a mutated type VII collagen comprising the step of preventing splicing of one or more exons which encode amino acid sequence of type VII collagen implicated in dysfunction of a mutated type VII collagen wherein said exons are selected from the group consisting of exon 73, 74 or 80 of the COL7A1 gene.

2. A synthetic antisense oligonucleotide complementary to a nucleic acid sequence of COL7A1 gene that is necessary for correct splicing of one or more exons which encode amino acid sequence of type VII collagen implicated in dysfunction of a mutated type VII collagen wherein said exons are selected from the group consisting of exon 73, 74 or 80 of the COL7A1 gene, and wherein said antisense oligonucleotide is selected from the group consisting of sequences ESE73.3 (SEQ ID NO :1), ESE73.7 (SEQ ID NO :2), SA+ESE-74 (SEQ ID NO :3), SA+ESE-74 R2063W (SEQ ID NO :4), ESE-74.2+SD (SEQ ID NO :5), ESE-80.3(SEQ ID NO :6) and ESE80-3 Q2170X (SEQ ID NO :7), and wherein said antisense oligonucleotide prevents said splicing of said one or more exons into an mRNA transcript of said nucleic acid sequence of COL7A 1 gene.

3. The synthetic antisense oligonucleotide according to claim 2 which is inserted in a vector.

4. A pharmaceutical composition comprising at least one synthetic antisense oligonucelotide according to claim 2.

5. A method of treating a patient suffering from Dystrophic Epidermolysis Bullosa comprising the step of
administering to the patient, in an amount sufficient to ameliorate symptoms of said Dystrophic Epidermolysis Bullosa, an antisense oligonucleotide complementary to a nucleic acid sequence of COL7A1 gene that is necessary for correct splicing of one or more exons which encode amino acid sequence of type VII collagen implicated in dysfunction of a mutated type VII collagen wherein said exons are selected from the group consisting of exon 73, 74 or 80of the COL7A1 gene.

6. The method of claim 5, wherein said antisense oligonucleotide is selected from the group consisting of sequences ESE73.3 (SEQ ID NO :1), ESE73.7 (SEQ ID NO :2), SA+ESE-74 (SEQ ID NO :3), SA+ESE-74_R2063W (SEQ ID NO :4), ESE-74.2+SD (SEQ ID NO :5), ESE-80.3 (SEQ ID NO :6) and ESE80-3_Q2170X (SEQ ID NO :7).

7. The synthetic antisense oligonucleotide of claim 2, wherein said synthetic antisense oligonucleotide is a type selected from the group consisting of oligodeoxyribonucleotide, oligoribonucleotide, morpholino, tricycle-DNA-antisense oligonucleotide, U7-mediated antisense oligonucleotide, peptide-conjugated antisense oligonucleotide and nanoparticle-complexed antisense oligonucleotide.

* * * * *

SEQUENCE LISTING

<160> NUMBER OF SEQ ID NOS: 7

<210> SEQ ID NO 1
<211> LENGTH: 30
<212> TYPE: RNA
<213> ORGANISM: Artificial
<220> FEATURE:
<223> OTHER INFORMATION: Synthetic oligonucleotide ESE73.3

<400> SEQUENCE: 1
ucuccacggu cgcccuucag cccgcguucu                              30

<210> SEQ ID NO 2
<211> LENGTH: 25
<212> TYPE: RNA
<213> ORGANISM: Artificial
<220> FEATURE:
<223> OTHER INFORMATION: Synthetic oligonucleotide ESE73.7

<400> SEQUENCE: 2
ucuccacggu cgcccuucag cccgc                                   25

<210> SEQ ID NO 3
<211> LENGTH: 25
<212> TYPE: RNA
<213> ORGANISM: Artificial
<220> FEATURE:
<223> OTHER INFORMATION: Synthetic oligonucleotide SA+ESE-74

<400> SEQUENCE: 3
ccuuucucuc cccguucucc cugaa                                   25

<210> SEQ ID NO 4
<211> LENGTH: 25
<212> TYPE: RNA
<213> ORGANISM: Artificial
<220> FEATURE:
<223> OTHER INFORMATION: Synthetic oligonucleotide SA+ESE-74_R2063W

<400> SEQUENCE: 4
ccuuucucuc cccauucucc cugaa                                   25

<210> SEQ ID NO 5
<211> LENGTH: 26
<212> TYPE: RNA
<213> ORGANISM: Artificial
<220> FEATURE:
<223> OTHER INFORMATION: Synthetic oligonucleotide ESE-74.2+SD

<400> SEQUENCE: 5
ccaccuguuc uccacguucu ccuuuc                                  26

<210> SEQ ID NO 6
<211> LENGTH: 24
<212> TYPE: RNA
<213> ORGANISM: Artificial
<220> FEATURE:
<223> OTHER INFORMATION: Synthetic oligonucleotide ESE-80.3

<400> SEQUENCE: 6
ggccucuugg acccugcaga cccu                                    24

<210> SEQ ID NO 7
<211> LENGTH: 24
<212> TYPE: RNA
<213> ORGANISM: Artificial
<220> FEATURE:
<223> OTHER INFORMATION: Synthetic oligonucleotide ESE80-3_Q2170X

<400> SEQUENCE: 7
ggccucuugg acccuacaga cccu                                    24